United States Patent [19]

Shaw, Jr.

[11] 4,427,110
[45] Jan. 24, 1984

[54] APPARATUS AND METHOD FOR HANDLING USED DISPOSABLE DIAPERS

[76] Inventor: Kenneth N. Shaw, Jr., c/o Samual Curcio, Esq., P.O. Box 593, Hammonton, N.J. 08037

[21] Appl. No.: 410,567

[22] Filed: Aug. 23, 1982

[51] Int. Cl.$^3$ .............................................. B65D 81/24
[52] U.S. Cl. .................... 206/205; 206/222; 220/87; 220/229; 220/402; 220/404
[58] Field of Search ............... 206/204, 205, 361, 222; 220/87, 229, 300, 301, 401, 402, 403, 404, 804

[56] References Cited

U.S. PATENT DOCUMENTS

| | | | |
|---|---|---|---|
| 51,264 | 11/1865 | Niles | 220/301 |
| 1,613,621 | 1/1927 | Oke | 220/404 |
| 1,659,726 | 2/1928 | Veider | 220/403 |
| 1,916,493 | 7/1933 | Soloman | 220/404 |
| 2,112,465 | 3/1938 | Maish | 220/401 |
| 2,308,398 | 1/1943 | Stevens | 220/401 |
| 2,733,052 | 1/1956 | Luther | 220/301 |
| 2,802,590 | 8/1957 | Tupper | 220/87 |
| 3,086,674 | 4/1963 | Scheuerman | 220/229 |
| 3,182,727 | 5/1965 | Minton | 220/88 |
| 3,268,104 | 8/1966 | Wei | 220/300 |
| 3,315,402 | 4/1967 | Scott et al. | 220/229 |
| 3,346,140 | 10/1967 | Mele | 220/87 |
| 3,451,540 | 6/1969 | Kulfschenko | 206/222 |
| 3,603,469 | 9/1971 | Magni | 206/222 |
| 3,620,399 | 11/1971 | Rapeaud | 220/404 |
| 3,862,595 | 1/1975 | Longo | 220/402 |
| 3,899,100 | 8/1975 | Rigaud | 220/229 |
| 4,053,084 | 10/1977 | Anderson | 220/229 |
| 4,311,237 | 1/1982 | Hayes | 220/401 |

FOREIGN PATENT DOCUMENTS 303,970 9/1968 Sweden ............................. 220/404

Primary Examiner—Joseph Man-Fu Moy
Attorney, Agent, or Firm—John H. Widdowson

[57] ABSTRACT

An apparatus for handling used disposable diapers having a canister base with a rim and a seal insert supported by the rim of the canister base. The seal insert has a structure defined by a plurality of radially disposed slits intersecting centrically to provide flexible sliced pre-shaped sectors adapted to be flexed downwardly into the top of the canister base by a downward force and to spring back into the plane of the seal insert upon release of the downward force. A top has a depending flange to average the seal insert against the rim of the canister bar, and a frustoconical plunger adapted to flex the sliced pre-shaped sector downward when forced thereagainst. A deodorant receptacle with a deodorant is connected to the top. The method comprises placing the used disposable diapers on top of the seal insert and plunging the used diaper through the pre-shaped sector.

3 Claims, 6 Drawing Figures

U.S. Patent  Jan. 24, 1984  Sheet 1 of 2  4,427,110
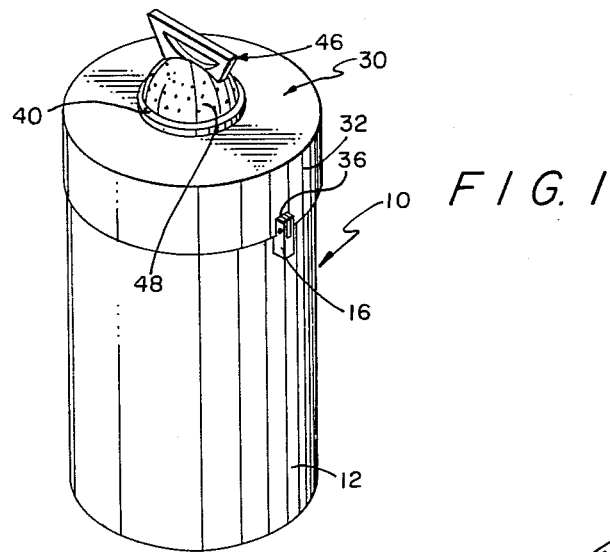
FIG. 1
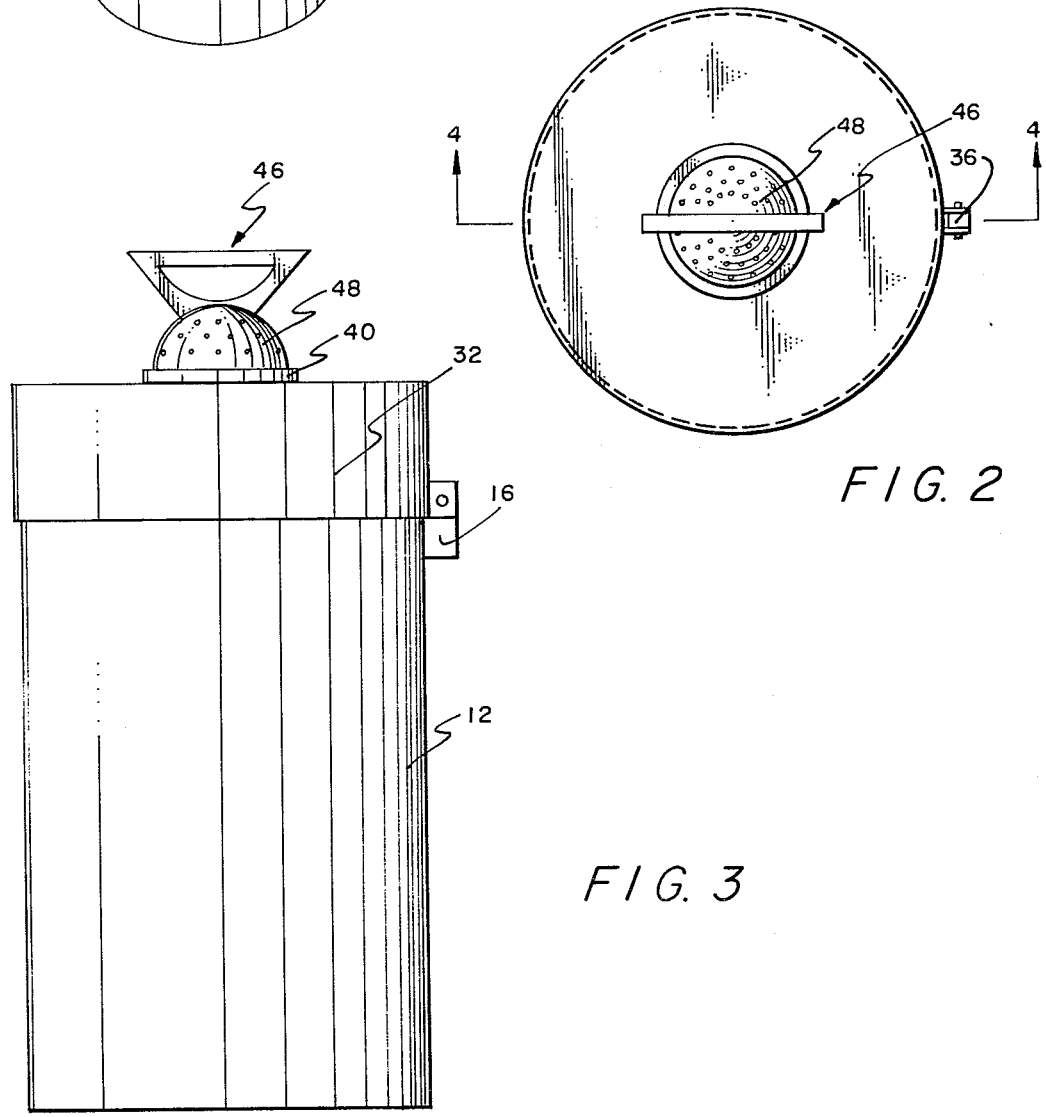
FIG. 2
FIG. 3

APPARATUS AND METHOD FOR HANDLING USED DISPOSABLE DIAPERS

BACKGROUND OF THE INVENTION

1. Field of the Invention

This invention relates to an apparatus and method for handling used disposable diapers. More specifically, this invention provides the apparatus and method for storing used diapers and deodorizing the area in proximity to the apparatus.

2. Description of Prior Art

U.S. Pat. No. 3,346,140 by Mele illustrates a diaper pail having a cover whereon the cover is provided with a container to hold a deodorant material. U.S. Pat. No. 3,307,902 by Wardi discloses a clothes hamper having a lid through which clothes may be passed. U.S. Pat. No. 3,749,274 by Mele et al teaches a diaper container having a lid through which diapers may be passed and carried on the underside thereof a container for a deodorant material. None of the foregoing prior art teaches the particular method and apparatus for handling used diapers of this invention.

SUMMARY OF THE INVENTION

This invention accomplishes its desired objects by providing an apparatus and method for handling used disposable diapers. The apparatus comprises a canister base means including a rim. A seal insert means is supported by the rim of the canister base and has a structure defined by a plurality of radially disposed slits intersecting generally centrically to provide flexible sliced pre-shaped sectors adapted to be flexed downwardly into the top of said canister base by a downward force and to spring back into the plane of the seal insert upon release of the downward force. A top means has a generally depending top flange to engage the seal insert means against the rim of the canister base and a generally frusto-conical plunger means integrally bound thereto and adapted to flex the sliced pre-shaped sectors downward when forced thereagainst. A deodorant receptacle means is bound to the top means. A deodorizer means is positioned within the receptacle means and a handle means engages the receptacle means and includes a perforate base for venting odors from the deodorizer means. The method comprises placing the used disposable diapers on top of the seal inserts and plunging the used diaper through the pre-shaped sectors.

It is an object of the inventor to provide a novel apparatus and method for handling used disposable diapers.

This together with the various ancillary objects and features will become apparent as the following description proceeds, are attained by this invention, preferred embodiments being shown in the accompanying drawings, by way of example only, wherein:

BRIEF DESCRIPTION OF THE DRAWINGS

FIG. 1 is a perspective view of the invention;

FIG. 2 is a top plan view of the invention;

FIG. 3 is an elevational view of the invention;

DETAILED DESCRIPTION OF THE INVENTION

Figure 5:
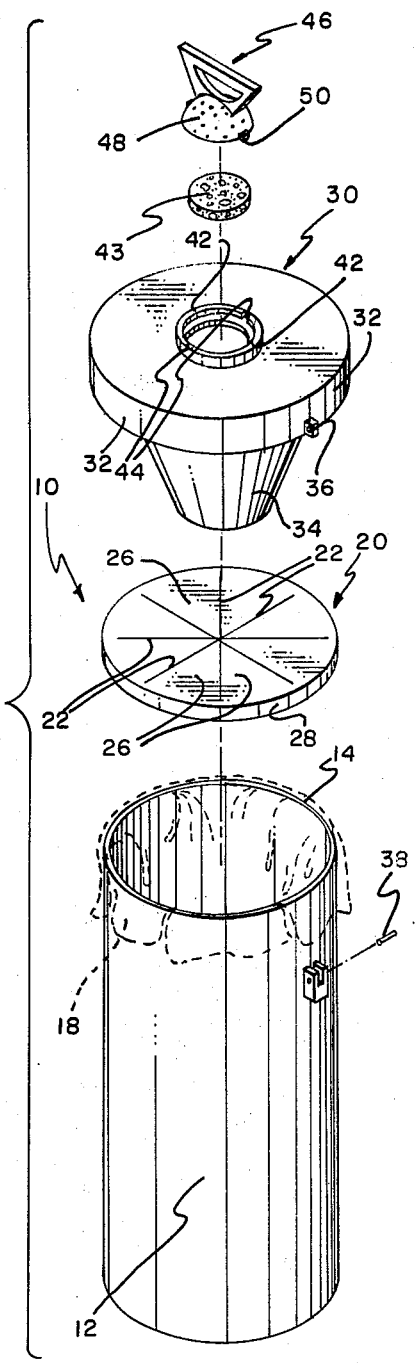
FIG. 5 is a segmented perspective view of the invention.

Referring in detail now to the drawings, wherein like reference numerals designate similar parts throughout the various views, there is seen the apparatus for handling used disposable diapers, generally illustrated as 10, having a canister base 12 including a rim 14 and a yoke 16. A disposable bag 18 removably lodges within the canister base 12 and overlaps over the rim 14 of the canister base 12 as illustrated in FIG. 5. A seal insert, generally illustrated as 20, is supported by the rim 14 of the canister base 12 and has a structure defined by a plurality of radially disposed slits 22 intersecting generally centrically at 24 to provide flexible sliced pre-shaped sectors 26 adapted to be flexed downwardly into the top of the canister base 12 by a downward force and to spring back into the plane of the seal insert 20 upon release of the downward force. The seal insert 20 additionally comprises a depending seal flange 28 to engage the overlapping bag 18 against the rim 14 of the canister base 12 and against the sides of the same in proximity to the rim 14. The depending seal flange 28 also prevents the insert 20 from sliding off the rim 14 of the canister base 12.

Figure 4:
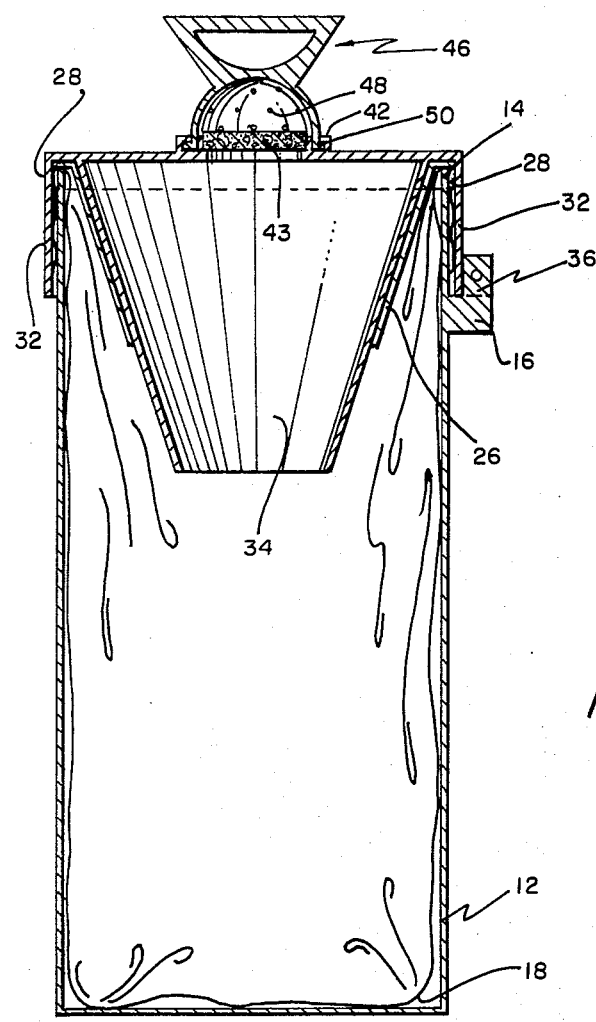
FIG. 4 is a vertical sectional view taken along the plane of line 4—4 and in direction of the arrows in FIG. 2.
Figure 6:
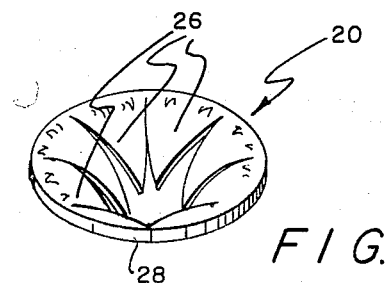
FIG. 6 is a perspective view of the seal insert with the sliced pre-shaped sectors flexed downwardly.

The apparatus 10 also includes a top, generally illustrated as 30, having a generally depending top flange 32 to engage the seal insert 20 including its seal flange 28 against the rim 14 of the canister base 12, and a generally frusto-conical plunger 34 integrally bound thereto and adapted to flex the sliced pre-shaped sectors 26 downward when forced thereagainst (see FIGS. 4 and 6). A hinge element 36 is bound to top flange 32. Element 36 inserts into yoke 16 and is secured therein by pin 38 (see FIG. 5) in order to pivot the top 30 about the yoke 16.

A deodorant receptacle 40 is integrally attached to the top 30 for receiving and holding a deodorizer means 43. Receptacle 40 includes a flanged perimeter 42 extending into the inside of the receptacle 40 for reducing the diameter of the same. The flanged perimeter 42 comprises a pair of diametrically opposed slots 44—44 (see FIG. 5).

A handle, generally illustrated as 46, includes a generally perforate base 48 for venting odors from the deodorizer means, and a pair of legs 50—50 bound to the bottom of the perforate base 48 and adapted for insertion through the slots 44—44 for lodging underneath the flanged perimeter 40 (see FIG. 4) of the deodorant receptacle when the handle 46 is rotated in order to secure the handle 46 to the deodorant receptacle 40.

With continuing reference to the drawings for operation of the invention and the method of handling used disposable diapers, the handle 46 is grasped and pulled upwardly to pivot the top 30 about the yoke 16 and disengage the plunger 34 from within the downwardly flexed sectors 26 which causes the sliced pre-shaped sectors 26 to spring back into the plane of the seal insert 20. Used disposable diapers (not shown in the drawings) are placed on the planes positioned sliced pre-shaped sectors 26 and the handle 46 is subsequently grasped to pivot the top 30 about the pin 38 in yoke 16 to downwardly flex the sliced pre-shaped sectors 26 and plunge the used diapers through the same when the frusto-conical plunger 34 of top 30 downwardly flexes the sectors 26. The deodorizer means 43 within the receptacle 40 deodorizes through perforate base 48 the contaminated air in proximity to the apparatus 10. After the bag 18 is filled with diapers it may be subsequently removed by lifting top 30 and removing insert seal 20 from around the rim 14 of the canister base 12. A new bag may subsequently be inserted. Also, when the deodorizer means 43 loses its strength a new deodorizer means 43 may be placed within the receptacle 40 by turning the handle 46 until bags 50—50 are aligned with slots 44—44 to remove the handle 46 away from the receptacle 40.

While the present invention has been described herein with reference to particular embodiments thereof, a latitude of modification, various changes and substitutions are intended in the foregoing disclosure, and it will be appreciated that in some instances some features of the invention will be employed without corresponding use of other features without departing from the scope of the invention as set forth.

I claim:

1. An apparatus for handling used disposable diapers comprising a canister base means including a rim;

a seal insert means supported by said rim of said canister base and having a structure defined by a plurality of radially disposed slits intersecting generally centrically to provide flexible sliced pre-shaped sectors adapted to be flexed downwardly into the top of said canister base by a downward force and to spring back into the plane of the seal insert upon release of the downward force;

a top means having a generally depending top flange to engage the seal insert means against the rim of said canister base means and a generally frusto-conical plunger means integrally bound thereto and adapted to flex the sliced pre-shaped sectors downward when forced thereagainst;

a deodorant receptacle means bound to said top means;

a deodorizer means positioned within said receptacle means; and a handle means engaged to said receptacle means and having a perforate base for venting odors from the deodorizer means, said deodorant receptacle means comprises a flanged perimeter extending into the receptacle for reducing the diameter of the receptacle means, said flanged perimeter including a pair of diametrically opposed slots, said handle means additionally comprises a pair of lugs bound to the bottom of said perforate base which are adapted for insertion through the slots for lodging underneath the flanged perimeter of the deodorant receptacle means when the handle means is rotated in order to secure the handle means to the deodorant receptacle means, the seal insert means additionally comprises a depending seal flange, said depending top flange additionally includes a hinge element means bound thereto, and said canister base comprises a yoke means secured to the sides thereof of securing said hinge element means to pivot the top means about said yoke means.

2. The apparatus of claim 1 additionally including a bag removably positioned into the canister base means and overlapping the rim thereof, said depending seal flange engaging the overlapping bag against the rim of the canister base and against the sides of same in proximity to the rim.

3. A method for handling used disposable diapers comprising the steps of:

(a) removing a top means from a canister base means, said top means includes a frusto-conical plunger means integrally bound thereto and a depending flange to engage a seal insert means against the rim of the canister base means;

(b) placing the used disposable diapers on the seal insert means supported by the rim of the canister base means and having a structure defined by a plurality of radially disposed slits intersecting generally centrically to provide flexible sliced pre-shaped sectors adapted to be flexed downwardly into the top of the canister base means by a downward force and to spring back into the plane of the seal insert means upon release of the downward force;

(c) plunging the used disposable diapers through the flexible pre-shaped sectors by forcing the frusto-conical plunger means of the top means against the sliced pre-shaped sectors to downwardly flex the sectors and allow the used diaper to free fall into the canister base;

deodorizing the contaminated air in proximity to the canister base by securing to said top means a perforate receptacle means for receiving a deodorizer means;

positioning a bag within the canister base for accumulating the diapers; and securing the bag to the rim of the canister base by the seal insert means having the sliced pre-shaped sectors.

* * * * *

UNITED STATES PATENT AND TRADEMARK OFFICE
CERTIFICATE OF CORRECTION

PATENT NO. : 4,427,110

DATED : January 24, 1984

INVENTOR(S) : Kenneth N. Shaw, Jr.

It is certified that error appears in the above-identified patent and that said Letters Patent is hereby corrected as shown below:

Claim 1 (Column 4, line 10) "of" should read -- for --.

Signed and Sealed this

Thirty-first Day of July 1984

[SEAL]

Attest:

GERALD J. MOSSINGHOFF

Attesting Officer     Commissioner of Patents and Trademarks